United States Patent
Zhang

(10) Patent No.: US 10,016,366 B2
(45) Date of Patent: Jul. 10, 2018

(54) METHOD OF PREPARING LYOPHILIZED POWDER FOR INJECTION COMPRISING ALOE AND PANAX PSEUDO-GINSENG

(71) Applicant: Rongxuan Zhang, Zhengzhou (CN)

(72) Inventor: Rongxuan Zhang, Zhengzhou (CN)

( * ) Notice: Subject to any disclaimer, the term of this patent is extended or adjusted under 35 U.S.C. 154(b) by 426 days.

(21) Appl. No.: 15/011,450

(22) Filed: Jan. 29, 2016

(65) Prior Publication Data

US 2016/0143853 A1 May 26, 2016

Related U.S. Application Data

(63) Continuation-in-part of application No. PCT/CN2013/001297, filed on Oct. 28, 2013.

(30) Foreign Application Priority Data

Sep. 28, 2013 (CN) .......................... 2013 1 0448923

(51) Int. Cl.
*A61K 9/19* (2006.01)
*A61K 9/00* (2006.01)
*A61K 36/258* (2006.01)
*A61K 36/886* (2006.01)

(52) U.S. Cl.
CPC .............. *A61K 9/19* (2013.01); *A61K 9/0019* (2013.01); *A61K 36/258* (2013.01); *A61K 36/886* (2013.01)

(58) Field of Classification Search
None
See application file for complete search history.

(56) References Cited

FOREIGN PATENT DOCUMENTS

| CN | 102090451 A | * | 6/2011 |
| CN | 102309667 A | * | 1/2012 |

OTHER PUBLICATIONS

English translation of CN102309667A (Google Patents). (Year: 2012).*
English translation of CN102090451A (Google Patents). (Year: 2011).*

* cited by examiner

*Primary Examiner* — Michael P Barker
(74) *Attorney, Agent, or Firm* — Matthias Scholl, PC; Matthias Scholl

(57) ABSTRACT

A method of preparing a lyophilized powder for injection, including: (1) weighing and mixing aloe powder and *Panax pseudo-ginseng* powder to yield an active pharmaceutical ingredient, and mixing the active pharmaceutical ingredient and distilled water to yield a mixed aqueous solution; (2) stiffing the mixed aqueous solution to enable the aloe power and the *Panax pseudo-ginseng* powder to be completely dissolved, and then allowing the mixed aqueous solution to stand; (3) collecting, filtering, and clarifying a supernate obtained in (2); (4) adding hydrochloric acid to a filtrate obtained in (3) to adjust the pH value of the filtrate, heating and sterilizing the filtrate, and then naturally cooling the filtrate, to yield a cooled liquid; (5) adding hydrochloric acid to the cooled liquid to adjust the pH value of the cooled liquid, filtering the cooled liquid and collecting a pharmaceutical solution; and (6) packaging and lyophilizing the pharmaceutical solution.

7 Claims, No Drawings

METHOD OF PREPARING LYOPHILIZED POWDER FOR INJECTION COMPRISING ALOE AND PANAX PSEUDO-GINSENG

CROSS-REFERENCE TO RELATED APPLICATIONS

This application is a continuation-in-part of International Patent Application No. PCT/CN2013/001297 with an international filing date of Oct. 28, 2013, designating the United States, now pending, and further claims priority benefits to Chinese Patent Application No. 201310448923.9 filed Sep. 28, 2013. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a method of preparing a lyophilized powder for injection for promoting the secretion of estrogen.

Description of the Related Art

Aloe and *Panax pseudo-ginseng* are well-known Chinese traditional medicinal materials.

SUMMARY OF THE INVENTION

It is one objective of the invention to provide a method of preparing a lyophilized powder for injection using aloe and *Panax pseudo-ginseng* as materials. The lyophilized powder for injection is capable of promoting the secretion of estrogen of mammals.

To achieve the above objective, in accordance with one embodiment of the invention, there is provided a method of preparing a lyophilized powder for injection, the method comprising:

(1) weighing and mixing between 50 and 99 parts by weight of aloe powder and between 1 and 50 parts by weight of *Panax pseudo-ginseng* powder to yield an active pharmaceutical ingredient, and mixing the active pharmaceutical ingredient and distilled water according to a weight ratio thereof of 100:2000 to yield a mixed aqueous solution;

(2) stifling the mixed aqueous solution to enable the aloe power and the *Panax pseudo-ginseng* powder to be completely dissolved, and then allowing the mixed aqueous solution to stand overnight;

(3) collecting, filtering, and clarifying a supernate obtained in (2);

(4) adding hydrochloric acid to a filtrate obtained in (3) to adjust a pH value of the filtrate to between 6.3 and 6.5, heating and sterilizing the filtrate at a temperature of between 110 and 120° C. for 30 min, and then naturally cooling the filtrate, to yield a cooled liquid;

(5) adding hydrochloric acid to the cooled liquid to adjust a pH value of the cooled liquid to between 4.2 and 4.5, filtering the cooled liquid using an ultrafiltration membrane and collecting a pharmaceutical solution with a molecular weight equal to or less than 10000 Da; and (6) packaging the pharmaceutical solution into ampoules and lyophilizing the pharmaceutical solution.

In a class of this embodiment, a weight ratio of the aloe power and the *Panax pseudo-ginseng* powder is 50:50.

In a class of this embodiment, a weight ratio of the aloe power and the *Panax pseudo-ginseng* powder is 70:30.

In a class of this embodiment, a weight ratio of the aloe power and the *Panax pseudo-ginseng* powder is 90:10.

In a class of this embodiment, a weight ratio of the aloe power and the *Panax pseudo-ginseng* powder is 99:1.

In a class of this embodiment, the aloe power is prepared according to following steps:

(a) soaking fresh aloe leaves for 30-60 min, washing, cleaning, and pulverizing the aloe leaves to yield aloe slurry;

(b) adding the aloe slurry to a heating reactor and introducing steam to the heating reactor to heat the aloe slurry to a temperature of between 8 and 12° C., adding a pectase or protease accounting for 0.125 wt. % of the aloe slurry, 50-60 min later, raising the temperature to between 75 and 80° C., and maintaining the temperature for between 3 and 5 hrs for sterilization treatment; and (c) filtering, concentrating, and drying a sterilized aloe solution obtained in (b) to yield a light yellow aloe powder.

In a class of this embodiment, the *Panax pseudo-ginseng* powder is prepared according to following steps:

(a) soaking *Panax pseudo-ginseng* for 30-60 min, washing, cleaning, and pulverizing the *Panax pseudo-ginseng* to yield superfine powders having particle sizes of between 0.02 and 15 μm; and (b) adding distilled water to dissolve the superfine powders according to a weight ratio thereof of 100:2000, adding a resulting solution to a heating reactor and introducing steam to the heating reactor to heat the solution to a temperature of between 75 and 80° C., maintaining the temperature for between 3 and 5 hrs, and concentrating and drying the solution to yield a light yellow *Panax pseudo-ginseng* powder.

Advantages of the method of preparing a lyophilized powder for injection according to embodiments of the invention are summarized as follows. The resulting lyophilized powder for injection is capable of promoting the secretion of estrogen of mammals and thus can substitute for the conventional male and female sex hormones, thereby avoiding toxicity and side effects.

DETAILED DESCRIPTION OF THE EMBODIMENTS

For further illustrating the invention, experiments detailing a method of preparing a lyophilized powder for injection are described below. It should be noted that the following examples are intended to describe and not to limit the invention.

The invention provides a method of preparing a lyophilized powder for injection. The lyophilized powder comprises aloe powder and *Panax pseudo-ginseng* powder and can promote the secretion of estrogen. The preparation process of the lyophilized powder is summarized as follows.

1. Preparation of Aloe Powder

Fresh aloe leaves were soaked for 30-60 min, and then were washed, cleaned and pulverized using a food-grade stainless steel crusher to yield aloe slurry. During pulverization, the skin of the aloe leaves was removed or pulverized together. The aloe slurry was added to a heating reactor and steam was introduced to the heating reactor to heat the aloe slurry to a temperature of between 8 and 12° C. A pectase or protease accounting for 0.125 wt. % of the aloe slurry was added to the slurry to accelerate the degradation of aloe. 50-60 min later, the temperature was raised to between 75 and 80° C., and maintained for between 3 and 5 hrs for sterilization treatment. The sterilized aloe solution was filtered using a screen vibrator, diatomite, or sheet frame, or a combination thereof. If decolorization was required, activated carbon can be added. After concentration (the soluble solid in the concentrate was controlled within 10%), the sterilized aloe solution was spray dried or lyophilized to yield a light yellow aloe powder.

2. Preparation of *Panax pseudo-ginseng* Powder

Soaking *Panax pseudo-ginseng* for 30-60 min, washing, cleaning, and pulverizing the *Panax pseudo-ginseng* to yield superfine powders having particle sizes of between 0.02 and 15 μm; adding distilled water to dissolve the superfine powders according to a weight ratio thereof of 100:2000, adding a resulting solution to a heating reactor and introducing steam to the heating reactor to heat the solution to a temperature of between 75 and 80° C., maintaining the temperature for between 3 and 5 hrs, and concentrating and drying the solution to yield a light yellow *Panax pseudo-ginseng* powder.

3. Preparation of Lyophilized Powder for Injection (1) Weighing and mixing between 50 and 99 parts by weight of the aloe powder and between 1 and 50 parts by weight of the *Panax pseudo-ginseng* powder to yield an active pharmaceutical ingredient, and mixing the active pharmaceutical ingredient and distilled water according to a weight ratio thereof of 100:2000 to yield a mixed aqueous solution. In practice, the mixing ratio of the aloe powder to the *Panax pseudo-ginseng* powder was 50:50, 70:30, 90:10 or 90:10.

(2) Uniformly stiffing or ultrasonically dissolving the mixed aqueous solution for 15 min to enable the aloe power and the *Panax pseudo-ginseng* powder to be completely dissolved, to yield a light brown solution, and then allowing the light brown solution to stand overnight (a high pressure homogenizer can be employed).

(3) Collecting, filtering, and clarifying a supernate obtained in (2).

(4) Adding 37% of hydrochloric acid to a filtrate obtained in (3) to adjust a pH value of the filtrate to between 6.3 and 6.5, heating and sterilizing the filtrate at a temperature of between 110 and 120° C. for 30 min, and then naturally cooling the filtrate, to yield a cooled liquid.

(5) Adding 37% of hydrochloric acid to the cooled liquid to adjust a pH value of the cooled liquid to between 4.2 and 4.5, filtering the cooled liquid using an ultrafiltration membrane and collecting a pharmaceutical solution with a molecular weight equal to or less than 10000 Da (In industrial production, an automatic membrane ultrafiltration equipment can be used. In laboratory, a No. 4 funnel is feasible).

(6) Packaging the pharmaceutical solution into ampoules (100 mL) and lyophilizing the pharmaceutical solution at −30° C. (an automatic vacuum freeze-drying machine can be used), to yield a lyophilized powder for injection capable of promoting the secretion of estrogen.

Prior to injection, the lyophilized powder for injection is diluted and dissolved with 0.9% of normal saline.

The lyophilized powder for injection capable of promoting the secretion of estrogen comprises the following two types:

1. Light brown lyophilized powder for injection made from peeled aloe, specification: each ampoule contains 0.75 g of soluble active ingredient of aloe, hereinafter referred to as J01.

2. Brown lyophilized powder for injection made from whole leave aloe, Specification: each ampoule contains 0.9 g of soluble active ingredient of aloe, hereinafter referred to as J02.

EXAMPLE

Estrogen-Like Activity of J01 and J02

1. Purpose

Based on the mice model with bilateral oophorectomy, the estrogen-like activity of J01 and J02 was studied.

2. Materials

Animal: Female ICR mice, weighed 18-22 g, provided by Nanjing Medical University Animal Experimental center, Animal certificate ID: SCXK (Su) 2013-0005.

J01, light brown lyophilized powder for injection, specification: each ampoule contains 0.75 g of soluble active ingredient of aloe. J02, brown lyophilized powder for injection, specification: each ampoule contains 0.9 g of soluble active ingredient of aloe. Upon administration, the powders for injection were dissolved and diluted with sterile normal saline to a desired concentration.

Diethylstilbestrol injection, specification: 1 : 3 mg, batch number: 20120516, provided by Shanghai General Pharmaceutical Co., Ltd.

3. Method 3.1 Healthy female ICR mice weighted 20±2 g were anaesthetized by ether and fixed in the abdomen. Bilateral ovaries of the mice were extirpated via back incision below the costal bone. The wounds were stitched and the mice were cultured according to conventional methods. After the wounds were cured, vaginal smear examination was performed, one time per day for five consecutive days, to ensure the ovaries were completely extirpated. The mice in the dioestrum (observations of vaginal smears under microscope found a lot of polynuclear leucocytes and few epithelial cells) in the five consecutive days were qualified mice. 48 mice were randomly divided into 6 groups with each group 8 mice, that is, a model group (be administered with equal volume of normal saline), a diethyl stilbestrol group (1 mg/kg), J01 groups (144 mg/kg, 288 mg/kg), J02 groups (180 mg/kg, 360 mg/kg). Another 6 mice with bilateral ovaries were selected as a control group (be administered with equal volume of normal saline). The mice were administered with corresponding drugs, one time per day, for 14 consecutive days. After one hour from the last injection, blood was sampled from the orbital venous plexus, and centrifuged for 10 min at 3000 rpm. The serum was separated and the E2, LH and FSH values thereof were measured using ELISA method. Thereafter, the abdominal cavity was cut open quickly and thymus, spleen, and uterus were separated and weighed to calculate the coefficients of the thymus, spleen, and uterus.

3.2 Administration Mode and Frequency

The mice were administered with corresponding drugs, 5 mL/kg, one time per day, for 14 consecutive days.

3.3 Evaluation Index

Viscera index: coefficients of the thymus, spleen, and uterus. Viscera index=organ weight/mice body weight*10. Serum index: E2 (estradiol), LH (luteinizing hormone), FSH (follicle stimulating hormone).

3.4 Statistical Method

The difference between groups of the measured data is examined based on ANOVA T-TEST using SPSS10.0.

4. Results

The index of uterus and E2 level of the ovariectomized female mice decreased significantly (p<0.01), while the LH and FSH level increased (p<0.01). After J01/J02 administration, the body character indexes of the mice varied differently. After two weeks when the J01 was administered to the mice, the index of uterus of the mice of the dosage groups of 144 mg/kg and 288 mg/kg increased significantly, and presented a significant difference compared to the model group (p<0.01) (as shown in Table. 1). Meanwhile, the E2 in the serum of the mice of the two dosage groups increased significantly (as shown in Table. 2). That is to say, J01 exhibited significant estrogen-like activity, and can promote the partial recovery of the female features of the ovariectomized mice. In addition, J01 can significantly reduce the serum LH level of female mice, compared with the model group, p<0.05 (as shown in Table. 3). J01 exhibited no significant influence on serum FSH (as shown in Table. 4).

After the J02 was administered to the mice, the index of uterus of the mice of the high dosage group (360 mg/kg) increased significantly, and presented a significant difference compared to the model group (p<0.05) (as shown in Table. 1), while the index of uterus of the mice of the low dosage group (180 mg/kg) had no significant change. In addition, with regard to the estradiol level, after the J02 was administered to the mice, the E2 level of the mice increased, which, however, presented no significant difference (p>0.05) compared to the model group (as shown in Table 2). Likewise, the LH and FSH level had no significant change (as shown in Tables 3 and 4). That is to say, J02 had no significant stimulation to the ovariectomized mice, and presents no significant estrogen-like activity.

5. Conclusion

J01 exhibits significant stimulation for the female organ (uterus) of the ovariectomized mice, and can partially recover the serum estrogen level, that is, has significant estrogen-like activity. Data show that only 360 mg/kg J02 exhibits certain stimulation for the female organ (uterus) of ovariectomized mice, and has almost no recovery capacity for the serum estrogen level.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

TABLE 1

Influence of J01 and J02 on viscera index of ovariectomized mice (M ± SD)

| Groups | Dosage (mg/kg) | Thymus index (mg/10 g) | Spleen index (mg/10 g) | Uterus index (mg/10 g) |
|---|---|---|---|---|
| Control group | — | 28.61 ± 8.31 | 55.27 ± 4.20 | 41.35 ± 8.71 |
| Model group | — | 30.90 ± 8.21 | 88.10 ± 1.94 | 28.72 ± 7.99$^{\$\$}$ |
| Diethylstilbestrol group | 1 mg/kg | 32.99 ± 8.11 | 66.67 ± 16.93 | 62.67 ± 11.89** |
| J01 low dose group | 144 | 26.60 ± 12.71 | 117.33 ± 33.84 | 45.98 ± 11.87** |
| J01 high dose group | 288 | 27.16 ± 11.90 | 136.44 ± 21.54 | 46.04 ± 16.41** |
| J02 low dose group | 180 | 31.69 ± 9.04 | 96.17 ± 15.61 | 30.26 ± 9.40 |
| J02 high dose group | 360 | 23.75 ± 10.24 | 109.28 ± 35.03 | 45.17 ± 24.02* |

TABLE 2

Influence of J01 and J02 on E2 of ovariectomized mice (M ± SD)

| Groups | Dose (mg/kg) | E2 (Estrogen) (pg/mL) |
|---|---|---|
| Control group | — | 126.35 ± 30.62 |
| Model group | — | 61.18 ± 18.76$^{\$\$}$ |
| Diethylstilbestrol group | 1 mg/kg | 113.81 ± 33.85 |
| J01 low dose group | 144 | 85.66 ± 27.39* |
| J01 high dose group | 288 | 96.05 ± 24.91** |
| J02 low dose group | 180 | 72.12 ± 20.61 |
| J02 high dose group | 360 | 80.82 ± 23.56 |

TABLE 3

Influence of J01 and J02 on LH of ovariectomized mice (M ± SD)

| Groups | Dose mg/kg | LH (luteinizing hormone) (ng/mL) |
|---|---|---|
| Control group | — | 13.27 ± 4.8 |
| Model group | — | 52.58 ± 5.77$^{\$\$}$ |
| Diethylstilbestrol group | 1 mg/kg | 31.33 ± 4.51 |
| J01 low dose group | 144 | 42.62 ± 5.13* |
| J01 high dose group | 288 | 37.71 ± 6.22* |
| J02 low dose group | 180 | 46.39 ± 7.45 |
| J02 high dose group | 360 | 47.87 ± 7.04 |

TABLE 4

Influence of J01 and J02 on FSH of ovariectomized mice (M ± SD)

| Groups | Dose (mg/kg) | FSH (Follicle Stimulating Hormone) (ng/mL) |
|---|---|---|
| Control group | — | 4.81 ± 1.35 |
| Model group | — | 32.23 ± 5.35$^{\$\$}$ |
| Diethylstilbestrol group | 1 mg/kg | 22.54 ± 6.97 |
| J01 low dose group | 144 | 30.15 ± 8.83 |
| J01 high dose group | 288 | 25.94 ± 7.41 |
| J02 low dose group | 180 | 33.17 ± 10.02 |
| J02 high dose group | 360 | 31.39 ± 9.77 |

The invention claimed is:

1. A method of preparing a lyophilized powder for injection, the method comprising:

(1) weighing and mixing between 50 and 99 parts by weight of aloe powder and between 1 and 50 parts by weight of *Panax pseudo-ginseng* powder to yield an active pharmaceutical ingredient, and mixing the active pharmaceutical ingredient and distilled water according to a weight ratio thereof of 100:2000 to yield a mixed aqueous solution;

(2) stifling the mixed aqueous solution to enable the aloe power and the *Panax pseudo-ginseng* powder to be completely dissolved, and then allowing the mixed aqueous solution to stand overnight;

(3) collecting, filtering, and clarifying a supernate obtained in (2);

(4) adding hydrochloric acid to a filtrate obtained in (3) to adjust a pH value of the filtrate to between 6.3 and 6.5, heating and sterilizing the filtrate at a temperature of between 110 and 120° C. for 30 min, and then naturally cooling the filtrate, to yield a cooled liquid;

(5) adding hydrochloric acid to the cooled liquid to adjust a pH value of the cooled liquid to between 4.2 and 4.5, filtering the cooled liquid using an ultrafiltration membrane and collecting a pharmaceutical solution with a molecular weight equal to or less than 10000 Da; and (6) packaging the pharmaceutical solution into ampoules and lyophilizing the pharmaceutical solution.

2. The method of claim 1, wherein the aloe power is prepared according to following steps:
(a) soaking fresh aloe leaves for 30-60 min, washing, cleaning, and pulverizing the aloe leaves to yield aloe slurry;
(b) adding the aloe slurry to a heating reactor and introducing steam to the heating reactor to heat the aloe slurry to a temperature of between 8 and 12° C., adding a pectase or protease accounting for 0.125 wt. % of the aloe slurry, 50-60 min later, raising the temperature to between 75 and 80° C., and maintaining the temperature for between 3 and 5 hrs for sterilization treatment; and
(c) filtering, concentrating, and drying a sterilized aloe solution obtained in (b) to yield a light yellow aloe powder.

3. The method of claim 1, wherein the *Panax pseudo-ginseng* powder is prepared according to following steps:

(a) soaking *Panax pseudo-ginseng* for 30-60 min, washing, cleaning, and pulverizing the *Panax pseudo-ginseng* to yield superfine powders having particle sizes of between 0.02 and 15 μm; and
(b) adding distilled water to dissolve the superfine powders according to a weight ratio thereof of 100:2000, adding a resulting solution to a heating reactor and introducing steam to the heating reactor to heat the solution to a temperature of between 75 and 80° C., maintaining the temperature for between 3 and 5 hrs, and concentrating and drying the solution to yield a light yellow *Panax pseudo-ginseng* powder.

4. The method of claim 1, wherein a weight ratio of the aloe power and the *Panax pseudo-ginseng* powder is 50:50.

5. The method of claim 1, wherein a weight ratio of the aloe power and the *Panax pseudo-ginseng* powder is 70:30.

6. The method of claim 1, wherein a weight ratio of the aloe power and the *Panax pseudo-ginseng* powder is 90:10.

7. The method of claim 1, wherein a weight ratio of the aloe power and the *Panax pseudo-ginseng* powder is 99:1.

* * * * *